(12) United States Patent
Ishizuka et al.

(10) Patent No.: US 9,370,762 B2
(45) Date of Patent: Jun. 21, 2016

(54) CHEMICAL REACTION APPARATUS

(71) Applicants: Microwave Chemical Co., Ltd., Osaka-shi, Osaka (JP); Osaka University, Osaka (JP)

(72) Inventors: Akinori Ishizuka, Osaka (JP); Iwao Yoshino, Osaka (JP); Kunitaka Momota, Osaka (JP); Yasunori Tsukahara, Osaka (JP)

(73) Assignee: MICROWAVE CHEMICAL CO., LTD., Osaka (JP)

( * ) Notice: Subject to any disclaimer, the term of this patent is extended or adjusted under 35 U.S.C. 154(b) by 0 days.

(21) Appl. No.: 14/357,172

(22) PCT Filed: Nov. 9, 2012

(86) PCT No.: PCT/JP2012/079153
§ 371 (c)(1),
(2) Date: Aug. 26, 2014

(87) PCT Pub. No.: WO2013/069779
PCT Pub. Date: May 16, 2013

(65) Prior Publication Data
US 2015/0004069 A1 Jan. 1, 2015

(30) Foreign Application Priority Data
Nov. 11, 2011 (JP) .................................. 2011-247955

(51) Int. Cl.
*B01J 19/12* (2006.01)
*C07C 67/03* (2006.01)
(Continued)

(52) U.S. Cl.
CPC .......... *B01J 19/126* (2013.01); *B01J 8/20* (2013.01); *B01J 8/36* (2013.01); *B01J 19/18* (2013.01); *B01J 19/1862* (2013.01); *C07C 67/03* (2013.01);
(Continued)

(58) Field of Classification Search
None
See application file for complete search history.

(56) References Cited

U.S. PATENT DOCUMENTS 3,463,627 A * 8/1969 LeBlanc ..................... 65/134.3
4,279,722 A    7/1981 Kirkbride
(Continued)

FOREIGN PATENT DOCUMENTS

CN  1729049      2/2006
CN  101954266 A  1/2011
(Continued)

OTHER PUBLICATIONS

Crespo, et al., "Extraction of Hydrocarbons from Seaweed Samples Using Sonication and Microwave—Assisted Extraction: A Comparative Study", Journal of Chromatographic Science, 2006, vol. 44, No. 10, p. 615-618.
(Continued)

*Primary Examiner* — Kishor Mayekar
(74) *Attorney, Agent, or Firm* — Troutman Sanders LLP

(57) ABSTRACT

A chemical reaction apparatus includes: a horizontal flow-type reactor inside of which has been partitioned into multiple chambers by a partition plate, and a liquid content horizontally flows with an unfilled space being provided thereabove; a microwave generator that generates microwaves; and at least one waveguide that transmits the microwaves generated by the microwave generator to the unfilled space in the reactor. The reactor has a shape in which an area of a liquid surface does not change even in a case where a height of the liquid surface changes according to a change in an amount of the content.

4 Claims, 21 Drawing Sheets

(51) Int. Cl.
*C07C 67/08* (2006.01)
*H05B 6/78* (2006.01)
*H05B 6/80* (2006.01)
*B01J 8/20* (2006.01)
*B01J 8/36* (2006.01)
*B01J 19/18* (2006.01)

(52) U.S. Cl.
CPC *C07C 67/08* (2013.01); *H05B 6/78* (2013.01); *H05B 6/806* (2013.01); *B01J 2208/00442* (2013.01); *B01J 2208/00867* (2013.01); *B01J 2219/00141* (2013.01); *B01J 2219/0877* (2013.01); *B01J 2219/0892* (2013.01); *B01J 2219/1218* (2013.01); *B01J 2219/1224* (2013.01); *B01J 2219/1227* (2013.01); *B01J 2219/1245* (2013.01); *B01J 2219/1266* (2013.01); *B01J 2219/1269* (2013.01); *B01J 2219/1275* (2013.01); *B01J 2219/1293* (2013.01); *B01J 2219/1296* (2013.01); *B01J 2219/182* (2013.01); *B01J 2219/187* (2013.01)

(56) References Cited

U.S. PATENT DOCUMENTS

| | | | |
|---|---|---|---|
| 4,844,838 | A | 7/1989 | Ohtsuka et al. |
| 5,393,320 | A | 2/1995 | Gomez |
| 5,458,897 | A | 10/1995 | Paré |
| 5,822,879 | A | 10/1998 | Vincent et al. |
| 6,723,999 | B2 | 4/2004 | Holl |
| 7,348,182 | B2 | 3/2008 | Martin |
| 8,328,997 | B2 | 12/2012 | Charlier de Chily et al. |
| 2004/0056026 | A1* | 3/2004 | Jakes et al. ............... 219/701 |
| 2006/0228088 | A1 | 10/2006 | Charlier De Chily et al. |
| 2006/0237300 | A1 | 10/2006 | Stroder et al. |
| 2007/0295717 | A1 | 12/2007 | Horikawa et al. |
| 2010/0025227 | A1 | 2/2010 | Charlier De Chily et al. |
| 2010/0172202 | A1* | 7/2010 | Borgstadt ..................... 366/15 |
| 2011/0263843 | A1 | 10/2011 | Watanabe et al. |
| 2013/0102804 | A1 | 4/2013 | Charlier De Chily et al. |

FOREIGN PATENT DOCUMENTS

| | | |
|---|---|---|
| EP | 0626871 B1 | 4/1997 |
| EP | 2727647 A1 | 5/2014 |
| JP | S 51-041679 | 4/1976 |
| JP | S52-35350 | 3/1977 |
| JP | S59-4431 | 1/1984 |
| JP | S 63-198899 | 8/1988 |
| JP | S 63-285121 | 11/1988 |
| JP | H 0266497 | 3/1990 |
| JP | H 03-109296 U | 11/1991 |
| JP | H 06-041545 | 2/1994 |
| JP | H 07-258117 | 10/1995 |
| JP | H07309433 A | 11/1995 |
| JP | H 08-501016 | 2/1996 |
| JP | H08242783 A | 9/1996 |
| JP | H09285282 A | 11/1997 |
| JP | H 1050470 | 2/1998 |
| JP | 2001009009 A | 1/2001 |
| JP | 2002-079078 | 3/2002 |
| JP | 2004-201967 | 7/2004 |
| JP | 2004-216200 | 8/2004 |
| JP | 2006-511775 | 4/2006 |
| JP | 2006-512554 | 4/2006 |
| JP | 2006-516008 | 6/2006 |
| JP | 2006-257304 | 9/2006 |
| JP | 2007-000774 | 1/2007 |
| JP | 2007-059317 | 3/2007 |
| JP | 2007-059318 | 3/2007 |
| JP | 2007-222696 | 9/2007 |
| JP | 2007-307440 | 11/2007 |
| JP | 2007-326013 | 12/2007 |
| JP | 2008-302281 | 12/2008 |
| JP | 2009-183198 | 8/2009 |
| JP | 2010-111865 | 5/2010 |
| JP | 2010-184230 | 8/2010 |
| JP | 2011-235262 | 11/2011 |
| JP | 2011-235263 | 11/2011 |
| WO | WO 93/14821 | 8/1993 |
| WO | WO 2004/056471 | 7/2004 |
| WO | 2004/066683 | 8/2004 |
| WO | WO 2005/102510 | 11/2005 |
| WO | WO 2006/109588 | 10/2006 |
| WO | WO 2009/110245 | 9/2009 |
| WO | WO 2009/149027 | 12/2009 |
| WO | 2010/013696 | 2/2010 |

OTHER PUBLICATIONS

Hattab, et al., "Comparison of various extraction methods for identification and determination of volatile metabolites from the brown alga Dictyopteris membranacea", Journal of Chromatography A, 2007, vol. 1143, p. 1-7.
Hattab, et al., "Isolation of the Volatile Compounds from the Brown Alga Dictyopteris membranacea by Focused Microwave-Assisted Hydrodistillation", J. Essent. Oil Res., 2002, vol. 14, No. 6, p. 422-424.
International Search Report dated Aug. 23, 2011, which issued during the prosecution of International Application No. PCT/JP2011/064965.
Itaya et al., "Effect of Scattering by Fluidization of Electrically Conductive Beads on Electrical Field Intensity Profile in Microwave Dryers" 2005, Drying Technology, 23, p. 273-287.
Japanese Office Action, dated Aug. 3, 2011, which issued during the prosecution of Japanese Patent Application No. 2010-111270.
Japanese Office Action, dated Oct. 31, 2013, which issued during the prosecution of Japanese Patent Application No. 2010-111271.
Japanese Search Report dated Jun. 2, 2010, prepared for Japanese Patent Application No. 2010-111271.
Japanese Search Report dated May 31, 2010, prepared for Japanese Patent Application No. 2010-111270.
Uy et al., "Seaweed processing using industrial single-mode cavity microwave heating: a preliminary investigation", Carbohydrate Research, 2005, vol. 340, No. 7, p. 1357-1364.
Written Opinion dated Aug. 23, 2011, which issued during the prosecution of International Application No. PCT/JP2011/064965.
International Search Report dated Jan. 29, 2013, from corresponding International Application No. PCT/JP2012/079153.
Ishizuka, A. et al. "Microwave Chemical Process: Process Innovation and Application" Fine Chemical, 2011, vol. 40, No. 3, pp. 42-46.
Chinese Office Action dated Oct. 30, 2014, which issued during prosecution of Chinese Application No. 201180071600.1.
Supplementary European Search Report dated Feb. 26, 2015 which issued during prosecution of EP Application No. 11868832.4.
Chinese Office Action dated Feb. 2, 2015 which issued during prosecution of CN Application No. 201280062762.3.
Office Action dated Apr. 1, 2015 which issued during prosecution of U.S. Appl. No. 14/357,145.
Chinese Office Action issued Sep. 22, 2015 during the prosecution of Chinese Patent Application No. 201280062750.0.
Chinese Office Action issued Sep. 22, 2015 during the prosecution of Chinese Patent Application No. 201280062762.3.
Japanese Office Action issued Nov. 25, 2015 during the prosecution of Japanese Patent Application No. 2012-522686.
Chinese Office Action dated Jun. 25, 2015, which issued during prosecution of Chinese Application No. 201180071600.1.
Office Action dated Jul. 9, 2015 which issued during prosecution of U.S. Appl. No. 13/807,865.
Extended European Search Report dated Jul. 13, 2015 which issued during prosecution of EP Application No. 12848355.9.
Extended European Search Report dated Jul. 20, 2015 which issued during prosecution of EP Application No. 12848048.0.
Office Action dated Aug. 18, 2015 which issued during prosecution of U.S. Appl. No. 14/357,145.
Chinese Office Action dated Mar. 4, 2016, issued in corresponding Application No. 2012800627623.

* cited by examiner

CHEMICAL REACTION APPARATUS

CROSS-REFERENCE TO RELATED APPLICATIONS

This is a U.S. national phase application under 35 U.S.C. §371 of International Patent Application No. PCT/JP2012/079153 filed on Nov. 9, 2012, and claims benefit of priority to Japanese Patent Application No. JP 2011-247955 filed on Nov. 11, 2011. The International Application was published on May 16, 2013, as International Publication No. WO 2013/069779 under PCT Article 21 (2). The entire contents of these applications are hereby incorporated by reference.

TECHNICAL FIELD

The present invention relates to a chemical reaction apparatus for irradiating microwaves in a reactor.

BACKGROUND ART

Conventionally, chemical reaction apparatuses and chemical reaction methods are known that perform heat treatment and the like by irradiating a reaction material with microwaves (electromagnetic waves) (see Patent Document 1, for example).

CITATION LIST

Patent Document

[Patent Document 1] JP 2006-516008A (Tokuhyo)

SUMMARY OF INVENTION

Technical Problem

In such conventional chemical reaction apparatuses, there has been a demand for further facilitating a chemical reaction by more efficiently irradiating microwaves.

The present invention was arrived at in view of these circumstances, and it is an object thereof to provide a chemical reaction apparatus capable of more efficiently irradiating a content with microwaves even in the case where the amount of the content changes in a horizontal flow-type reactor.

Solution to Problem

In order to achieve the above-described object, the present invention is directed to a chemical reaction apparatus, including: a horizontal flow-type reactor inside of which has been partitioned into multiple chambers by a partition plate, and a liquid content horizontally flows with an unfilled space being provided thereabove; a microwave generator that generates microwaves; and at least one waveguide that transmits the microwaves generated by the microwave generator to the unfilled space in the reactor; wherein the reactor has a shape in which an area of a liquid surface does not change even in a case where a height of the liquid surface changes according to a change in an amount of the content.

With this configuration, even in the case where the amount of content in the reactor changes and the height of the liquid surface increases or decreases, the area of the liquid surface that is irradiated with microwaves does not change. As a result, the area subjected to microwave irradiation does not decrease according to the increase or decrease in the height of the liquid surface, and the content can be efficiently irradiated with microwaves.

Furthermore, the chemical reaction apparatus of the present invention may be such that the reactor has a shape in which the area of the liquid surface does not change according to a change in the amount of the content, as long as the amount of the content is within a predetermined range.

With this configuration, the area of the liquid surface of a content does not change, for example, as long as the amount of the content is within a range between a first amount and a second amount (assuming that the second amount is larger than the first amount). Accordingly, the area of the liquid surface that is irradiated with microwaves does not change, by controlling the amount of the content in the reactor to be within that range.

Furthermore, the chemical reaction apparatus of the present invention may be such that the reactor has a shape in which a cross-section in a liquid surface direction of the content does not change, as long as the amount of the content is within the predetermined range.

Furthermore, the chemical reaction apparatus of the present invention may further include at least one agitation unit that rotationally agitates the content inside the reactor.

With this configuration, a content is agitated, and, thus, the content inside the reactor can be more uniformly irradiated with microwaves. As a result, for example, a situation can be avoided in which only part of the content inside the reactor is irradiated with microwaves.

Furthermore, the chemical reaction apparatus of the present invention may be such that the agitation unit includes: a rotational shaft that extends in a flow direction in the reactor; at least one rotatable member that is rotated about the rotational shaft; and a rotating unit that rotates the at least one rotatable member; and the reactor has a shape in which a cross-sectional area in the liquid surface direction does not change above the rotational shaft.

With this configuration, for example, even if the rotational shaft is made of a material not suitable for microwave irradiation, direct microwave irradiation on the rotational shaft can be avoided, and the area subjected to microwave irradiation can be prevented from changing, by controlling the amount of content such that the liquid surface of the content is above the rotational shaft.

Furthermore, the chemical reaction apparatus of the present invention may be such that the reactor has, below the rotational shaft, a semicylindrical shape elongated in the flow direction and projecting downward.

With this configuration, for example, in the case where the semicylindrical shape has a radius in accordance with the radius of the rotatable member, efficient agitation can be performed below the rotational shaft, and the locations not subjected to agitation can be reduced.

Furthermore, the chemical reaction apparatus of the present invention may be such that the reactor can be opened and closed above the unfilled space.

With this configuration, accessing the inside of the reactor becomes easy.

Advantageous Effects of Invention

The present invention provides a chemical reaction apparatus in which the area subjected to microwave irradiation does not change even in the case where the amount of content changes, as long as the amount of the content is within a predetermined range in a horizontal flow-type reactor. As a result, the content can be more efficiently irradiated with microwaves.

DESCRIPTION OF EMBODIMENT

Figure 1:
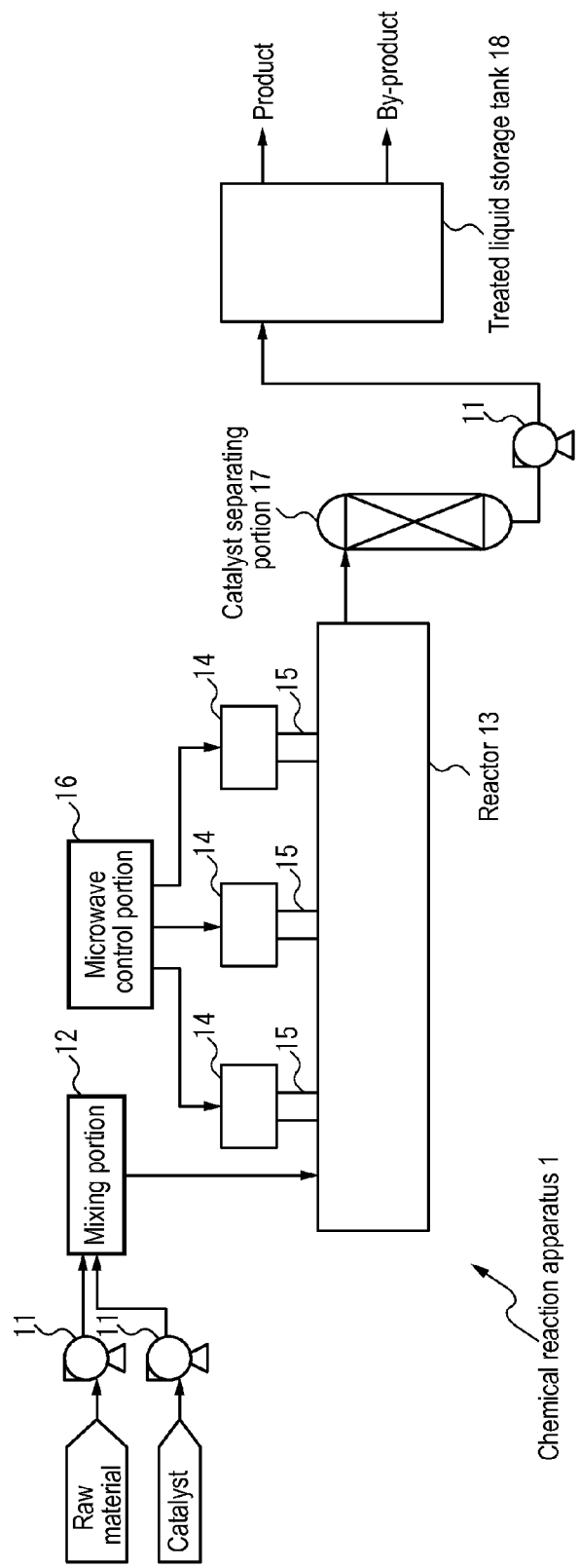
FIG. 1 is a diagram showing the configuration of a chemical reaction apparatus according to Embodiment 1 of the present invention.

Hereinafter, a chemical reaction apparatus according to the present invention will be described by way of an embodiment. Note that constituent elements denoted by the same reference numerals are the same or similar to each other in the following embodiment, and, thus, a description thereof may not be repeated.

Embodiment 1

Below, a chemical reaction apparatus according to Embodiment 1 of the present invention will be described with reference to the drawings. The chemical reaction apparatus according to this embodiment irradiates the content of a reactor with microwaves.

FIG. 1 is a diagram showing the configuration of a chemical reaction apparatus 1 according to this embodiment. The chemical reaction apparatus 1 according to this embodiment includes a mixing portion 12, a reactor 13, microwave generators 14, waveguides 15, a microwave control portion 16, a catalyst separating portion 17, and a treated liquid storage tank 18.

The mixing portion 12 mixes a raw material and a solid catalyst. The mixing portion 12 may mix the raw material and the like with a reactant. The raw material may contain multiple materials. For example, in the case of performing esterification in the reactor 13, fat and oils and alcohol may be used as the raw material. The raw material and the solid catalyst may be supplied to the mixing portion 12 by pumps 11 as shown in FIG. 1, or may be supplied to the mixing portion 12 using other methods. The mixing portion 12 may mix two or more materials, for example, by rotating a blade-like member, a wing-like member, or a screw-like member. Note that, although this embodiment describes the case in which the catalyst that is to be mixed with the raw material is a solid catalyst (heterogeneous catalyst), the catalyst may be a liquid catalyst (homogeneous catalyst). Furthermore, the solid catalyst may or may not form a fluidized bed inside the reactor 13. Furthermore, there is no limitation on the shape of the solid catalyst. Examples of the shape of the solid catalyst include various grains, a cylinder (that may or may not be hollow), a sphere, a pellet, a ring, a shell, and other shapes. Furthermore, the solid catalyst may or may not be, for example, microwave-absorbing or microwave-sensitive. If the solid catalyst is microwave-absorbing or microwave-sensitive, when microwaves are irradiated inside the reactor 13 (described later), the solid catalyst is heated by the microwaves, and the chemical reaction near the solid catalyst is facilitated. Note that the microwave absorptivity and the microwave sensitivity depend on the frequency of microwaves used for irradiation, the temperature inside the reactor 13, and the like. That is to say, materials that have a high dielectric loss factor, at the frequency of microwaves used and the temperature inside the reactor 13 in which the raw material is to undergo a reaction, provide a high microwave absorptivity. Accordingly, for example, a solid catalyst containing such a highly microwave-absorbing material may be used. For example, if microwaves at 2.45 GHz are irradiated, examples of the microwave-absorbing material include carbon except for fullerene (e.g., graphite, carbon nanotube, activated carbon, etc.), iron, nickel, cobalt, ferrite, and the like. Accordingly, the solid catalyst may contain such a microwave-absorbing material. Specifically, the solid catalyst may be a composite in which such a microwave-absorbing or microwave-sensitive material and a metal or metal oxide are combined, a composite in which such a microwave-absorbing or microwave-sensitive material and a catalyst such as alkali catalyst or acid catalyst are combined, or a composite in which a microwave-absorbing or microwave-sensitive material, a catalyst such as alkali catalyst or acid catalyst, and a metal or metal oxide are combined. The composite may be formed, for example, through physical adsorption, chemical bonding, alloying, or other methods. Furthermore, in the mixing portion 12, preliminary heating may or may not be performed for preparation for the reaction in the reactor 13. In the case of performing the preliminary heating, the temperature in the preliminary heating in the mixing portion 12 is preferably controlled such that the raw material and the like at the time of entering the reactor 13 are at a desired temperature or in a desired temperature range. Note that, in the case of not performing the preliminary heating in the mixing portion 12, heating corresponding to the preliminary heating may be performed in the reactor 13. The raw material and the solid catalyst mixed by the mixing portion 12 are loaded into the upstream side in the reactor 13.

The reactor 13 is a horizontal flow-type reaction unit in which a liquid content horizontally flows with an unfilled space being provided thereabove. Examples of the content include a mixture of the raw material and the catalyst. The raw material and the catalyst mixed by the mixing portion 12 flow inside the reactor 13. Note that, since the chemical reaction in the reactor 13 produces a product material from the raw material, the content of the reactor 13 may be considered to contain the product material. That is to say, the content may be referred to as the raw material and/or the product material. Furthermore, since an unfilled space is present above the content, the content is typically a material other than gas. Furthermore, the content can flow inside the reactor 13 and has a flat liquid surface, and, thus, the content is a material other than solid (e.g., powders or grains, etc.). Accordingly, the content is liquid. The liquid content may be for example, a material having a high flowability such as water, oil, aqueous solution, or colloidal solution, or may be a material having a low flowability such as slurry or suspension. It is preferable that the liquid surface of the content inside the reactor 13 is kept horizontal, and, thus, even in the case where the flowability of the liquid content is low, it preferably allows the liquid surface to be horizontal after a while without the application of vibration from the outside. That is to say, the liquid content preferably has a flowability that allows the shape of the surface to be changed without vibration from the outside. Note that the liquid surface being horizontal may refer to the state of being completely flat, or may refer to the state of being flat on the whole although there are slightly rough portions. The reason for this is that, if the content does not have a high flowability, the liquid surface may not be completely flat. The inner wall of the reactor 13 is preferably made of a microwave-reflecting material. Examples of the microwave-reflecting material include metal. The internal configuration of the reactor 13 will be described later.

The microwave generators 14 generate microwaves. The chemical reaction apparatus 1 according to this embodiment may include one microwave generator 14, or may include two or more microwave generators 14. There is no limitation on the frequency of the microwaves, and examples thereof include 2.45 GHz, 5.8 GHz, 24 GHz, 913 MHz, and other frequencies ranging from 300 MHz to 300 GHz.

The one or more waveguides 15 transmit the microwaves generated by the microwave generators 14 to the unfilled space in the reactor 13. The number of waveguides 15 provided may be the same as the number of microwave generators 14 as shown in FIG. 1. Furthermore, the waveguide 15 may be branched and transmit the microwaves to two or more positions in the unfilled space. Note that the specification of the waveguides 15 is preferably in accordance with the frequency of the microwaves generated by the microwave generators 14.

The microwave control portion 16 controls the power of microwaves used for irradiation in the reactor 13, according to the temperature measured by temperature measuring portions 25 (described later). The control by the microwave control portion 16 makes it possible to keep inside the reactor 13 at a desired temperature or in a desired temperature range.

The catalyst separating portion 17 separates the catalyst from the product material after the reaction in the reactor 13. If the catalyst that has been mixed with the raw material is a solid catalyst, for example, filtering may be used to separate the solid catalyst, or one of the solid catalyst and the product material may be precipitated to separate the solid catalyst. Furthermore, if the solid catalyst contains a magnetic substance, a magnet (that may be a permanent magnet or may be an electromagnet) for attracting the solid catalyst may be used to separate the solid catalyst. Note that the separated solid catalyst may be used again as appropriate. Furthermore, if a liquid catalyst is used, distillation, extraction, or neutralization may be performed in the catalyst separating portion 17 to separate the catalyst.

The product material from which the catalyst has been separated by the catalyst separating portion 17 is loaded into the treated liquid storage tank 18. Then, this product material is separated as appropriate into a final product, a by-product, and the like. For example, if the raw material is free fatty acid, and esterification is performed in the reactor 13, a product that is biodiesel fuel and a by-product that is water are obtained. In this case, an acid catalyst is used. Furthermore, for example, if the raw material is triglyceride, and transesterification is performed in the reactor 13, a product that is biodiesel fuel and a by-product that is glycerin are obtained. In this case, an alkali catalyst is used.

Note that an unshown cooler that cools down the material after the reaction in the reactor 13 may or may not be provided on the path after the reactor 13. In the former case, for example, the cooler may use water to cool down the material after the reaction in the reactor 13.

Figure 2:
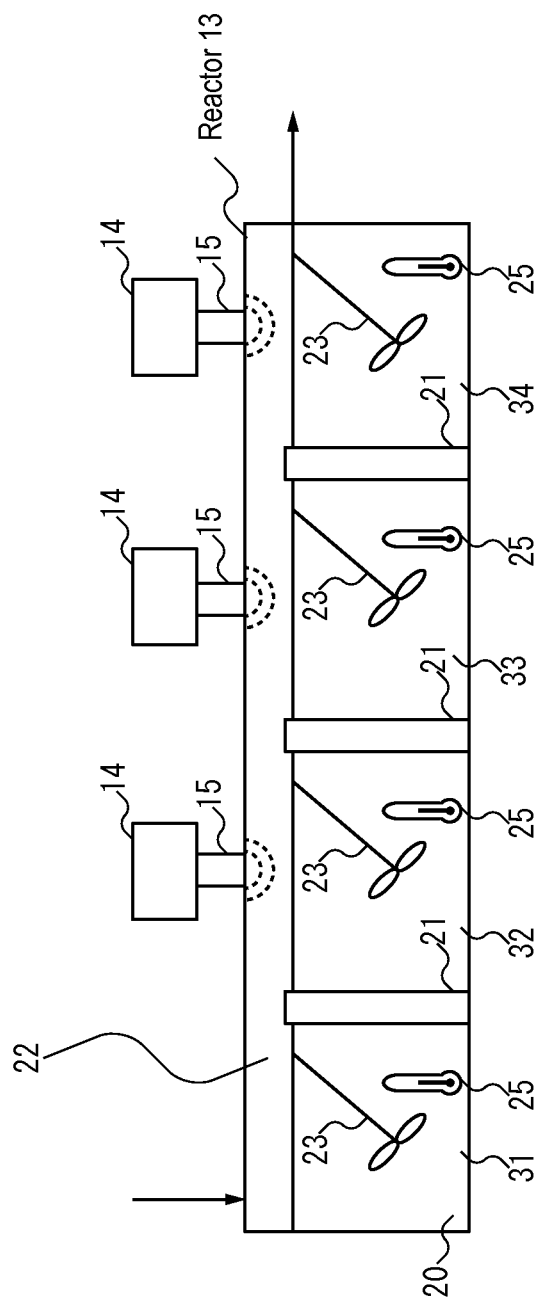
FIG. 2 is a view showing an exemplary internal configuration of a reactor according to the embodiment.

FIG. 2 is a view showing an exemplary internal structure of the reactor 13 according to this embodiment. In FIG. 2, the inside of the reactor 13 is partitioned by partition plates 21 into multiple chambers 31, 32, 33, and 34. The multiple chambers 31, 32, 33, and 34 are chambers that are continuously arranged in series. As described above, an unfilled space 22 is present in the upper portion inside the reactor 13. The unfilled space 22 is irradiated with the microwaves generated by the microwave generators 14 and transmitted via the waveguides 15. Note that FIG. 2 shows the case in which a single unfilled space is present inside the reactor 13, that is, the case in which an unfilled space is shared by all the chambers 31 to 34, but there is no limitation to this. That is to say, an unfilled space may be shared by at least two or more chambers that are part of all chambers, or may be shared by none of the chambers (in this case, there are unfilled spaces that have been separated from each other by the partition plates 21). The waveguides 15 may or may not be provided respectively at the positions around the middle in the chambers 32, 33, and 34 as shown in FIG. 2. In the former case, for example, the microwaves that have been transmitted by one waveguide 15 to the unfilled space 22 are mainly irradiated on the chamber present therebelow. Since microwaves are transmitted through an unfilled space, for example, the microwaves that have been transmitted by the waveguide 15 at the position of the chamber 32 are irradiated via the unfilled space also on the content in the chamber 31 and the chamber 33. Note that the waveguides 15 may be provided at the positions of the partition plates 21, that is, at the positions above the partition plates 21. Accordingly, the microwaves that have been transmitted by one waveguide 15 to the unfilled space 22 are mainly irradiated on two chambers that have been partitioned from each other by the partition plate 21 at the position corresponding to that waveguide 15. If the unfilled space is shared by multiple chambers, the microwaves that have been transmitted to the shared unfilled space are irradiated on a content 20 in the multiple chambers sharing the unfilled space. The partition plates 21 may transmit microwaves, may absorb microwaves, or may reflect microwaves. Examples of the microwave-transmitting material include Teflon (registered trademark), quartz glass, ceramic, silicon nitride-alumina, and the like. Accordingly, the partition plates 21 that transmit microwaves may be made of such a microwave-transmitting material. Furthermore, examples of the microwave-absorbing material include carbon except for fullerene, and the like. Accordingly, the partition plates 21 that absorb microwaves may be made of such a microwave-absorbing material. Furthermore, examples of the microwave-reflecting material include metal. Accordingly, the partition plates 21 that do not transmit microwaves may be made of such a microwave-reflecting material. Furthermore, the partition plates 21 may be made of a combination of two or more freely selected from the microwave-transmitting material, the microwave-absorbing material, and the microwave-reflecting material.

Furthermore, as shown in FIG. 2, the chemical reaction apparatus 1 may further include agitation units 23. That is to say, the chemical reaction apparatus 1 according to this embodiment may include one or more agitation units 23 that rotationally agitate the content 20 inside the reactor 13. FIG. 2 shows the case in which the chambers 31 to 34 respectively have the agitation units 23, but there is no limitation to this. One or more chambers may not have the agitation unit 23. Furthermore, FIG. 2 shows the case in which each of the agitation units 23 is in the shape of a blade, but this merely schematically shows the agitation units 23. The agitation may be performed, for example, by rotating a blade-like, wing-like, or rod-like rotatable member. The rotatable member may be made of a microwave-transmitting material, a microwave-absorbing material, a microwave-reflecting material, or a combination of two or more freely selected from the microwave-transmitting material, the microwave-absorbing material, and the microwave-reflecting material. The rotation may be performed, for example, by rotating a rotatable member attached to a shaft in accordance with the rotation of the shaft, or by rotating the rotatable member using a magnetic force as in the case of a magnetic stirrer. In the former case, the shaft may be provided independently for each chamber, or may be shared by multiple chambers. In the latter case, the rotatable member (magnetic stirrer) in the shape of a rod, a blade, a wing, or the like is rotated by a magnet. The agitation of the content by the agitation units 23 may be used to cause the content to flow from the upstream side to the downstream side, or in the opposite direction, but there is no limitation to this. Note that rotational agitation is already known, and, thus, a detailed description thereof has been omitted.

Hereinafter, reasons why the content of the reactor 13 is rotationally agitated by the agitation units 23 will be briefly described. A first reason why the content is agitated by the agitation units 23 is to uniformly heat the content with microwaves. Although depending on the type of content and the temperature of the content, the depth to which microwaves penetrate is fixed, and, thus, the agitation is performed in order to uniformly irradiate and uniformly heat the entire content with microwaves. Furthermore, the content can be more efficiently irradiated with microwaves as the surface area of the content at the unfilled space 22 increases. Accordingly, a second reason why the content is agitated is to increase the area subjected to microwave irradiation. Thus, the content is agitated by the agitation units 23 preferably at an intensity that allows the surface of the content at the unfilled space 22 to be disordered, but there is no limitation to this (if the agitation is performed for the first reason, it may be sufficient that the entire content is eventually heated). Furthermore, since the raw material and the like are agitated using the agitation units 23 in this manner, even in the case where a raw material contains two or more materials having different densities, these materials can be mixed and reacted with each other as appropriate. For example, when causing materials having different densities, such as alcohol and waste oil, to react with each other in a vertical flow-type reactor, these materials are easily separated from each other.

However, as in this embodiment, if the reactor 13 is of a horizontal flow-type and is provided with the agitation units 23, these materials can be mixed and reacted with each other as appropriate.

Furthermore, as shown in FIG. 2, the reactor 13 also may have the temperature measuring portions 25. That is to say, the chemical reaction apparatus 1 according to this embodiment may have the temperature measuring portions 25 that measure the temperature inside the reactor 13. The temperature inside the reactor 13 is preferably the temperature of the content of the reactor 13. FIG. 2 schematically shows the case in which the chambers 31 to 34 respectively have the temperature measuring portions 25, but there is no limitation to this. One or more chambers may not have the temperature measuring portion 25. Furthermore, FIG. 2 merely schematically shows the temperature measuring portions 25. The temperature measuring portions 25 may measure the temperature, for example, using a thermocouple, an infrared sensor, an optical fiber, or other methods. The temperature measured by the temperature measuring portions 25 (strictly speaking, data indicating the temperature) is passed to the microwave control portion 16, and is used to control the power of microwaves from the microwave generators 14. As described above, this control may be control for keeping the temperature of the chambers 31 to 34 at a desired temperature or in a desired temperature range. For example, if microwaves are irradiated on the position of each partition plate 21, the power of microwaves irradiated on that position may be controlled, for example, using one or both of the temperatures of two chambers that have been partitioned from each other by the partition plate 21 at the position subjected to the microwave irradiation. In the former case, for example, the control may be performed using a lower temperature, using a higher temperature, or using a temperature of a chamber specified in advance. In the latter case, for example, the control may be performed using an average of these temperatures, or using a weighted average according to the capacities of both chambers (average in consideration of weights according to the capacities of the chambers).

Figure 3A:
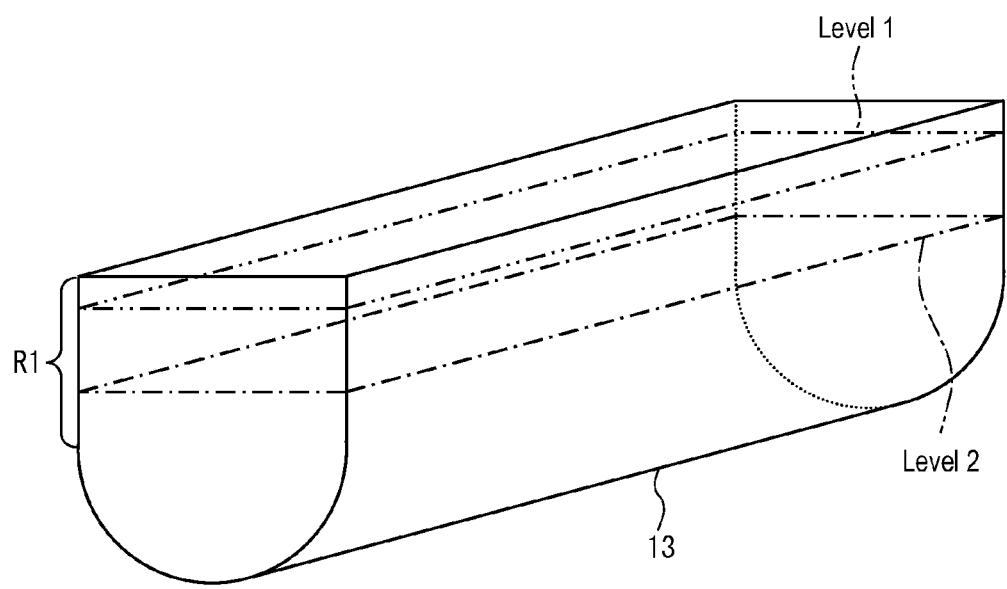
FIG. 3A is a perspective view showing an exemplary shape of the reactor according to the embodiment.
Figure 3B:
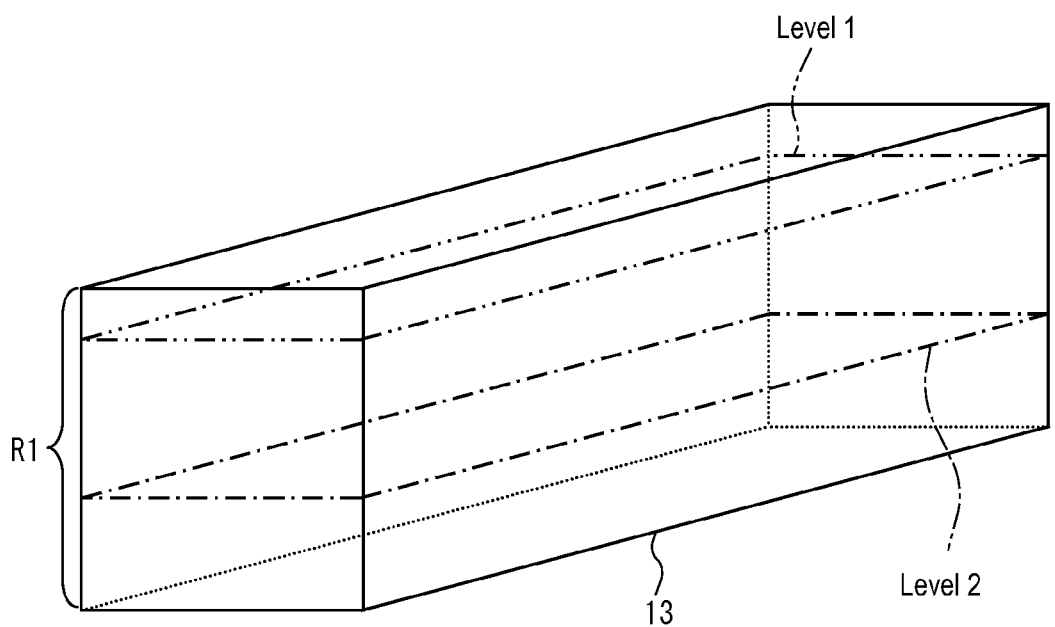
FIG. 3B is a perspective view showing an exemplary shape of the reactor according to the embodiment.

FIGS. 3A and 3B are views showing an exemplary shape of the reactor 13 according to this embodiment. In FIGS. 3A and 3B, the partition plates 21, the agitation units 23, and the like have been omitted for the sake of convenience of the description. In FIGS. 3A and 3B, the reactor 13 according to this embodiment has a shape in which the area of the liquid surface does not change even in the case where the height of the liquid surface changes according to a change in the amount of the content. Note that "the area of the liquid surface does not change even in the case where the height of the liquid surface changes according to a change in the amount of the content" refers to that there is at least the range of the content within which the area of the liquid surface does not change even in the case where the amount of the content changes. Accordingly, it is conceivable that the area of the liquid surface does not change according to the amount of the content regardless of the amount of the content, or that the area of the liquid surface does not change according to the amount of the content as long as the amount of the content is within a predetermined range, that is, as long as the amount of the content is between a first amount and a second amount (assuming that the second amount is larger than the first amount). In this embodiment, the latter case will be mainly described. That is to say, in this embodiment, the reactor 13 has a shape in which the area of the liquid surface does not change according to a change in the amount of the content as long as the amount of the content is within a predetermined range. Accordingly, the reactor 13 may have a shape in which the cross-section in the liquid surface direction of the content does not change as long as the amount of the content is within a predetermined range, for example, as shown in FIGS. 3A and 3B. In this case, within the range of the height of the liquid surface when the amount of the content changes from the first amount to the second amount, the shape in the horizontal direction inside the reactor 13 corresponding to the height of the liquid surface does not change. Note that the above-described first amount is typically the lower limit value of the content in the case where the area of the liquid surface does not change, and the second amount is typically the upper limit value of the content in the case where the area of the liquid surface does not change. Furthermore, even when the content is at the second amount, an unfilled space has to be present above the content. The reason for this is that microwaves are irradiated via an unfilled space in the reactor 13. Furthermore, the liquid surface may be disordered when agitation is performed inside the reactor 13 as described above, but the liquid surface described here is the liquid surface without such disorder or the like. Note that "the height of the liquid surface" is the height of the liquid surface in the vertical direction.

In FIG. 3A, the reactor 13 has a semicylindrical shape elongated in the flow direction and projecting downward. That is to say, the reactor 13 in FIG. 3A has a shape in which an open-topped semicylinder projecting downward and an open-bottomed rectangular solid having the same length as the semicylinder are joined at their openings. Note that the opening of the semicylinder and the opening of the rectangular solid have the same size and the same shape, and they are joined at their openings to form the reactor 13. In other words, the reactor 13 in FIG. 3A has a hollow shape having a side face with a U-shaped cross-section and an upper face with a cross-section closing the opening of the U-shape, wherein the openings at both ends of the hollow shape are closed by flat faces perpendicular to the length direction. In the reactor 13 in FIG. 3A, the area of the liquid surface does not change as long as the height of the liquid surface of the content is within a range R1 (e.g., the heights at a level 1, at a level 2, etc.). Note that the height of the liquid surface at the lowest level in the range R1 corresponds to the lowest position in the rectangular solid forming the upper portion of the reactor 13.

In FIG. 3B, the reactor 13 is in the shape of a rectangular solid. In the reactor 13 in FIG. 3B, the area of the liquid surface does not change as long as the height of the liquid surface of the content is within the range R1, which covers the entire height (e.g., the heights at the level 1, at the level 2, etc.). That is to say, the area of the liquid surface does not change regardless of the amount of the content.

Figure 4A:
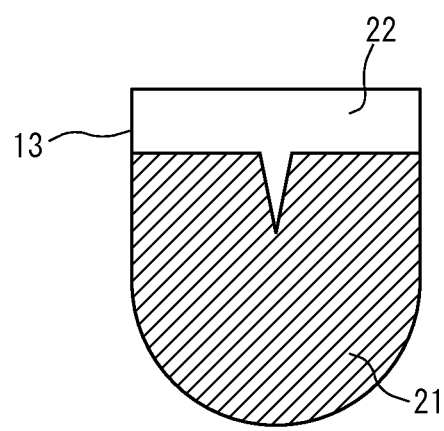
FIG. 4A is a view showing an exemplary shape of a partition plate according to the embodiment.
Figure 4B:
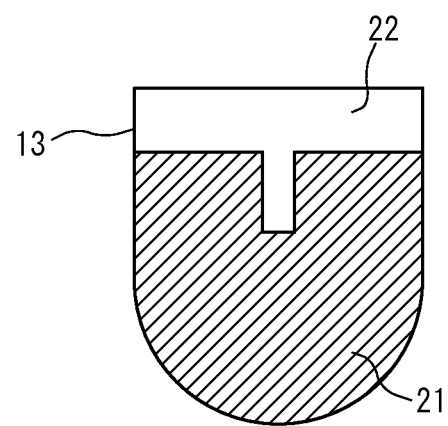
FIG. 4B is a view showing an exemplary shape of the partition plate according to the embodiment.
Figure 4C:
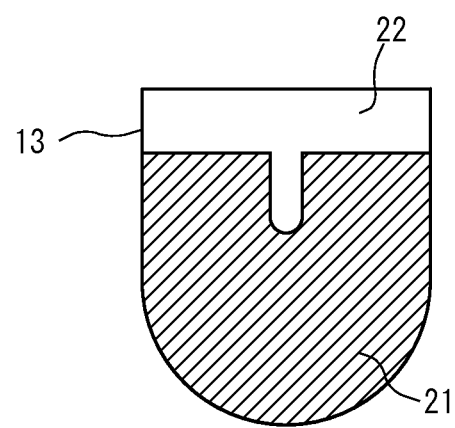
FIG. 4C is a view showing an exemplary shape of the partition plate according to the embodiment.
Figure 4D:
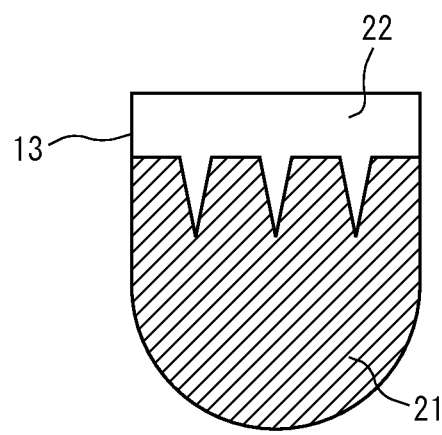
FIG. 4D is a view showing an exemplary shape of the partition plate according to the embodiment.
Figure 4E:
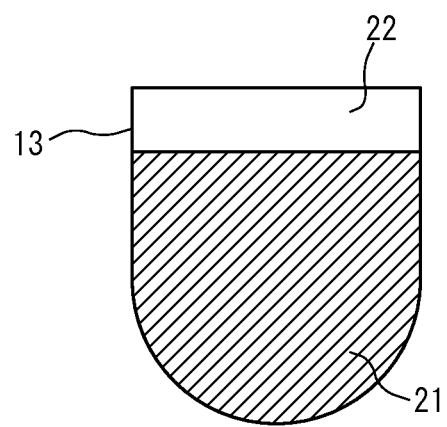
FIG. 4E is a view showing an exemplary shape of the partition plate according to the embodiment.
Figure 4F:
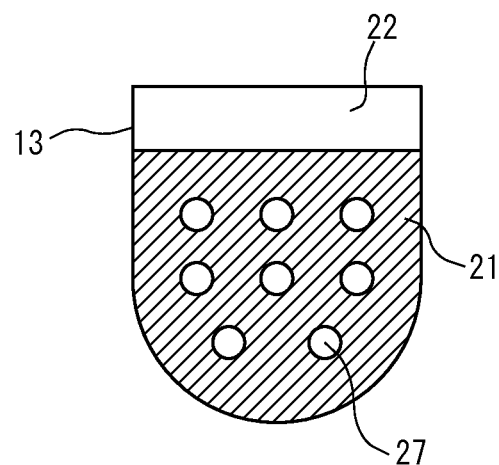
FIG. 4F is a view showing an exemplary shape of the partition plate according to the embodiment.
Figure 4G:
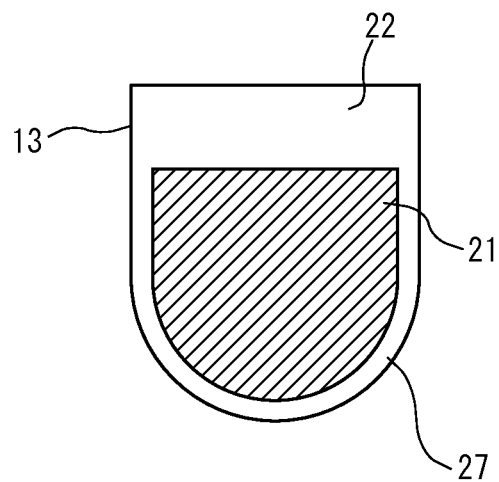
FIG. 4G is a view showing an exemplary shape of the partition plate according to the embodiment.
Figure 4H:
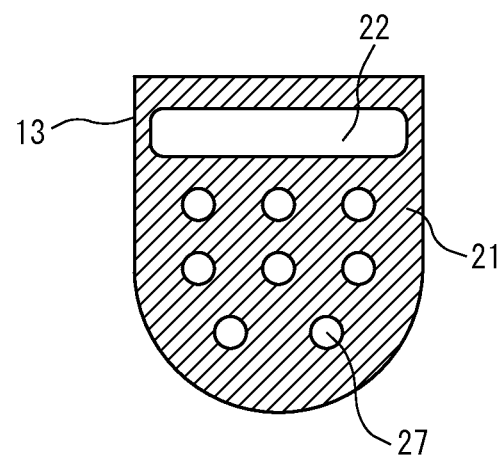
FIG. 4H is a view showing an exemplary shape of the partition plate according to the embodiment.

Next, the partition plates 21 will be described. The content 20 such as a raw material loaded into the reactor 13 flows through the chambers 31 to 34 and is finally discharged from the downstream side (the right end of the reactor 13 in FIG. 2). Note that a flow path that allows the content to flow is formed at the partition plates 21. The flow path allows the content to flow mainly from the upstream side (the left side in FIG. 2) to the downstream side (the right side in FIG. 2) in the reactor 13, but may allow part of the content to flow from the downstream side to the upstream side. The flow path at the partition plates 21 may be, for example, a flow path that allows the content to flow over the partition plates 21, or may be a flow path that allows the content to flow through a void of the partition plates 21. FIGS. 4A to 4H are views showing the partition plate 21 provided in the reactor 13 in the shape as shown in FIG. 3A, in the length direction of the reactor 13. For example, FIGS. 4A to 4E show the former type of partition plate 21, that is, the partition plate 21 having an overflow-type flow path. The partition plate 21 does not extend to the position of the unfilled space 22, and the content flows through that position (that is, over the partition plate 21). The overflow-type flow path may be a V-shaped flow path (triangular weir) as shown in FIG. 4A, may be a rectangular flow path (quadrangular weir) as shown in FIG. 4B, or may be a U-shaped flow path as shown in FIG. 4C. Furthermore, the number of flow paths may be one as shown in FIGS. 4A to 4C, or may be two or more as shown in FIG. 4D. FIG. 4D shows the case in which all of the multiple flow paths have the same shape, but there is no limitation to this. The multiple flow paths may have different shapes. Furthermore, the number of multiple flow paths may be two, or may be three or more. Furthermore, the flow path may have a shape other than those described in the drawings. For example, the flow path may be semicircular, may be trapezoidal, or may be in other shapes. Furthermore, the partition plate 21 may have a shape as in FIG. 4E in which the partition plate 21 has, on the upper side thereof, no recess such as cutout (portion that has been cut out), and a flow path is formed throughout the width of the reactor 13 (full-width weir). Furthermore, for example, FIGS. 4F to 4H show the partition plate 21 having a flow path formed as a void. In this case, for example, a void 27 may be present between the partition plate 21 and the inner wall of the reactor 13 as shown in FIG. 4G, or voids 27 may be present in the partition plate 21 itself as shown in FIGS. 4F and 4H. Each void 27 preferably has a size that at least allows the content to flow through the void. Note that there is no limitation on the shape and the number of voids 27. FIG. 4G shows the case in which the void 27 is U-shaped, but examples of the shape of the void 27 include a partially closed U shape. Furthermore, FIGS. 4F and 4H shows the case in which each of the voids 27 is in the shape of a circle, but examples of the shape of the voids 27 include a triangle, a rectangle, and other shapes. Furthermore, the number of voids 27 may be, for example, larger than or smaller than that shown in FIGS. 4F and 4H (i.e., may be one or may be two or more). Even in the case where a flow path is formed as a void as shown in FIGS. 4F to 4H, when the amount of the content increases, the content flows over the partition plate as well. Furthermore, the partition plate 21 may not extend to the upper side in the unfilled space 22 as shown in FIGS. 4A to 4G, or may partially extend to the upper side in the unfilled space 22 as shown in FIG. 4H. In the case of FIG. 4H, the unfilled space 22 is shared by multiple chambers via the opening in the upper portion of the partition plate 21. Although FIGS. 4A to 4H each show a partition plate in the case where the unfilled space 22 is shared by two chambers that have been partitioned from each other by that partition plate 21, the partition plate 21 may extend also to the position of the unfilled space 22, in the case where the unfilled space 22 is not shared. It will be appreciated that, if the reactor 13 has a shape other than that in FIG. 3A, the partition plate 21 is shaped in accordance with that shape of the reactor 13. Furthermore, if there are multiple partition plates 21 inside the reactor 13, the partition plates 21 may have the same shape, or may have different shapes.

Note that the height of the liquid surface inside the reactor 13 is on the whole determined by the position of the outlet of the reactor 13. Typically, the height of the liquid surface is higher than the position of the outlet, and, thus, the lower limit of the liquid surface can be determined by the position of the outlet. Furthermore, the height of the liquid surface in each chamber is determined by the height of the flow path between that chamber and a next chamber adjacent thereto. In this case, typically, the height of the liquid surface in each chamber is approximately the same as the position of the flow path through which the content flows out from that chamber, and, thus, the height of the liquid surface can be controlled by the position of that flow path. Typically, the height of the outlet from the reactor 13 is approximately the same as height of the flow path through which the content flows out from each chamber to the next chamber.

Figure 5A:
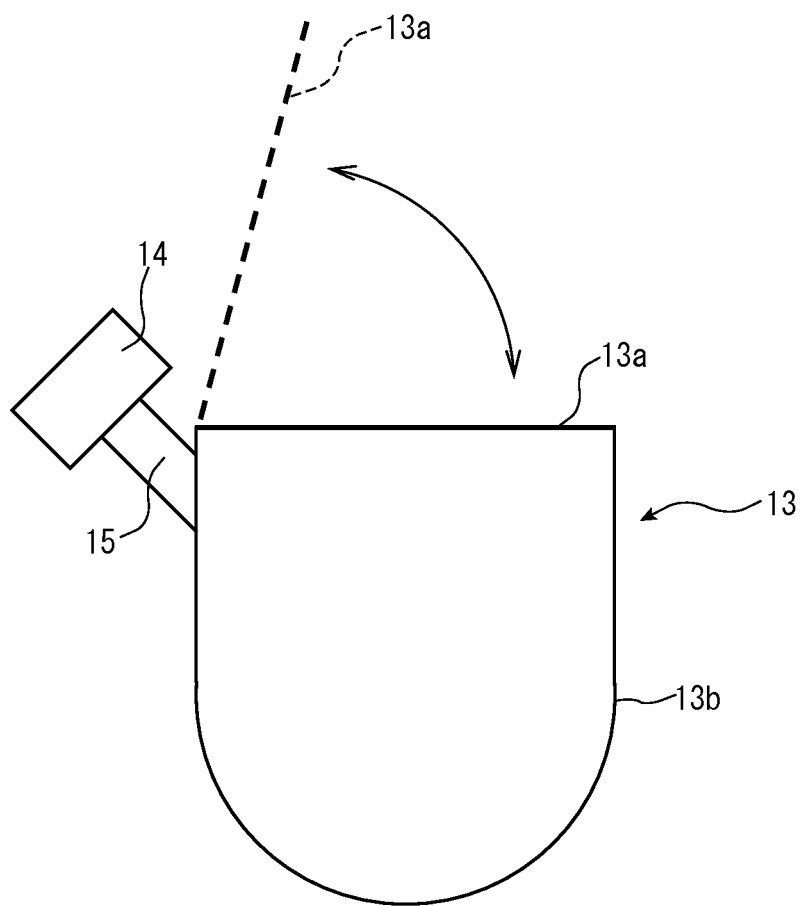
FIG. 5A is a view illustrating an opening and closing mechanism of the reactor according to the embodiment.

Furthermore, the reactor 13 may be made openable and closable above the unfilled space 22. In that case, for example, as shown in FIG. 5A, an upper face plate 13a of the reactor 13 may be provided openable and closable with respect to the opening at the top of a container portion 13b in the reactor 13. Specifically, the upper face plate 13a may be provided rotatable with respect to the container portion 13b about a hinge (shaft) in the length direction of the reactor 13. It is preferable that, when the opening at the top is closed by the upper face plate 13a, microwaves do not leak from a gap between the upper face plate 13a and the container portion 13b. Accordingly, for example, it is preferable that the opening at the top and the upper face plate 13a have the same shape (e.g., a rectangular shape, etc.), and there is no gap formed when the opening at the top is closed by the upper face plate 13a. Note that, in the case where the upper face plate 13a of the reactor 13 can be opened and closed, the waveguides 15 may transmit microwaves to the unfilled space 22 via the upper face plate 13a, or may transmit microwaves to the unfilled space 22 via the side face of the reactor 13. The latter configuration is better because it is preferable not to open and close the face provided with the waveguides 15. In this case, the reactor 13 being openable and closable refers to the configuration in which the reactor 13 is provided with a lid member that can be opened and closed. The lid member may be, for example, the upper face plate 13a, may be a door-like member, or may be another openable and closable member.

Figure 5B:
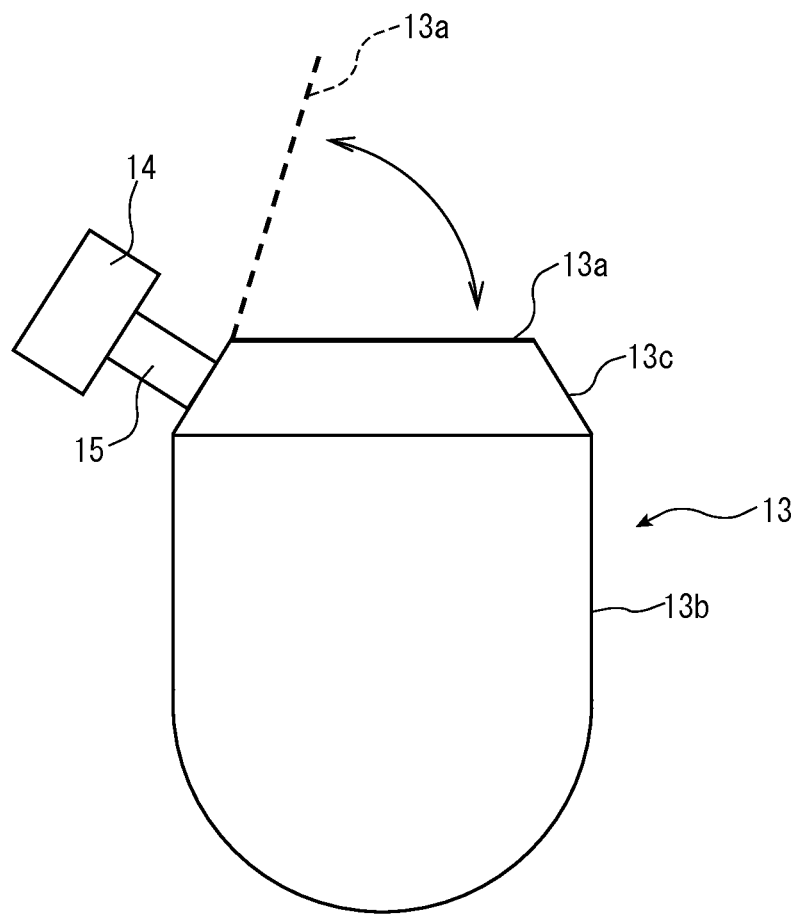
FIG. 5B is a view illustrating an opening and closing mechanism of the reactor according to the embodiment.

Furthermore, for example, as shown in FIG. 5B, the reactor 13 may further include a surrounding portion 13c that extends upward from the upper end of the container portion 13b so as to reduce the opening, and the upper face plate 13a of the reactor 13 may be provided openable and closable with respect to the opening at the top of the surrounding portion 13c. Specifically, the upper face plate 13a may be provided rotatable with respect to the surrounding portion 13c about a hinge in the length direction of the reactor 13. It is preferable that, when the opening at the top is closed by the upper face plate 13a, microwaves do not leak from a gap between the upper face plate 13a and the surrounding portion 13c. Accordingly, for example, it is preferable that the opening at the top and the upper face plate 13a have the same shape (e.g., a rectangular shape, etc.), and there is no gap formed when the opening at the top is closed by the upper face plate 13a. Note that, in the case where the upper face plate 13a of the reactor 13 can be opened and closed, the waveguides 15 may transmit microwaves to the unfilled space 22 via the upper face plate 13a, may transmit microwaves to the unfilled space 22 via the surrounding portion 13c, or may transmit microwaves to the unfilled space 22 via the side face of the reactor 13.

If the reactor 13 can be opened and closed above the unfilled space in this manner, for example, maintenance of the reactor 13 can be easily performed. In particular, if the reactor 13 can be opened and closed above the unfilled space 22, the content does not leak even when the upper face plate 13a is opened in a state where the content is in the reactor 13. Accordingly, it is possible to access the inside of the reactor 13 in a state where the content is in the reactor 13. Furthermore, since the reactor 13 is made openable and closable above the unfilled space for the purpose of accessing the inside of the reactor 13, such as checking the state inside the reactor 13 or performing maintenance of the internal portion, the opening that can be opened and closed preferably has a length approximately the same as the length in the length direction of the reactor 13, but there is no limitation to this.

Furthermore, the wall face of the reactor 13 may be covered by a heat insulating material. In that case, heat inside the reactor 13 can be prevented from being dissipated to the outside.

Next, an operation of the chemical reaction apparatus 1 according to this embodiment will be briefly described. The raw material and the catalyst are supplied by the pumps 11 to the mixing portion 12, are mixed in the mixing portion 12, and are loaded into the reactor 13. The speed of the raw material and the like supplied to the reactor 13 may be determined in advance.

The raw material and the like supplied to the reactor 13 flow from the upstream side to the downstream side while being agitated by the agitation units 23. At that time, the microwaves generated by the microwave generators 14 are transmitted via the waveguides 15 to the unfilled space 22 in the reactor 13, and are irradiated on the raw material and the like. As a result, the raw material and the like are heated, and the reaction of the raw material and the like is facilitated. Note that the temperatures of the chambers 31 to 34 are measured by the temperature measuring portions 25, and are passed to the microwave control portion 16 via a route that is not shown. Then, the microwave control portion 16 controls the power of the microwave generators 14 such that the temperatures of the chambers 31 to 34 are at a desired temperature or in a desired temperature range.

The product material discharged from the reactor 13 is loaded into the catalyst separating portion 17 where the catalyst is separated therefrom. Then, the product material from which the catalyst has been separated is loaded by the pump 11 into the treated liquid storage tank 18. In the treated liquid storage tank 18, the product material is separated into a target product and a by-product. In this manner, a final product is obtained. Furthermore, such treatment is repeatedly performed, and, thus, a target product is sequentially produced. During that treatment, even in the case where the amount of the content inside the reactor 13 increases or decreases, the area subjected to microwave irradiation does not change as long as the height of the liquid surface is within the above-described range R1. As a result, microwaves are efficiently irradiated. Furthermore, if the reactor 13 can be opened and closed above the unfilled space as shown in FIGS. 5A and 5B, for example, when checking the state inside the reactor 13 or performing maintenance of the internal portion of the reactor 13, it is possible to access the inside of the reactor 13 by opening the upper face plate 13a.

Note that the treatment that separates the catalyst in the catalyst separating portion 17 and the treatment that separates the product material into a product and a by-product in the treated liquid storage tank 18 may be performed sequentially each time the product material is loaded, or may be performed at a time when the amount of product material loaded accumulates and reaches a certain amount. That is to say, the treatment in the reactor 13 is of a flow-type (flow through-type), but the treatment in the catalyst separating portion 17 and the treated liquid storage tank 18 on the path thereafter may be of a flow-type, or may be of a batch-type.

Furthermore, there is no limitation on the chemical reaction caused to occur in the chemical reaction apparatus 1 according to this embodiment, as long as it is a chemical reaction that is caused to occur by microwave irradiation itself or by heat due to microwave irradiation. For example, the chemical reaction may be production of biodiesel fuel through esterification or transesterification, may be production of ink raw material that is ester, or may be other chemical reactions.

The treatment that produces biodiesel fuel (fatty acid methyl ester) from waste oil using the chemical reaction apparatus 1 according to this embodiment will be described by way of examples. It will be appreciated that the present invention is not limited to these examples.

Reaction System Construction Example

In this example, as the raw material, a mixture of fat and oils and free fatty acid, and alcohol were used. The alcohol was used as a reactant. The raw material and the catalyst were sent by the pumps 11 into the mixing portion 12, and were uniformly mixed. The mixed liquid was supplied to the reactor 13. The mixed liquid inside the reactor 13 was irradiated with the microwaves generated by the microwave generators 14, and, thus, the esterification reaction was facilitated. Furthermore, the mixed liquid inside the reactor 13 was loaded into the chambers 31 to 34 that had been partitioned from each other by the partition plates 21 inside the reactor 13. The mixed liquid together with the catalyst was irradiated with microwaves while being agitated by the agitation units 23, and, thus, the reaction progresses. The microwaves were irradiated on the unfilled space 22 inside the reactor 13, and were diffused inside the reactor 13. The reaction liquid in each chamber moved to its next chamber through a flow path provided at the partition plates 21. The reaction liquid was held inside the reactor 13 for a certain retention time, and then was discharged out of the reactor 13. The mixed liquid after the reaction discharged out of the reactor 13 was supplied to the catalyst separating portion 17. After the catalyst was separated in the catalyst separating portion 17, the mixed liquid was loaded into the treated liquid storage tank 18. From the reaction liquid after the catalyst separation, water and glycerin that were by-products were further separated in the treated liquid storage tank 18, and, thus, crude methyl ester that was a target product was obtained.

Esterification Reaction of Industrial Waste Oil

Hereinafter, a typical example of an esterification reaction of free fatty acid using industrial waste oil will be described. Industrial waste oil containing 34 wt % of free fatty acid (also containing triglyceride, pitch fraction, and the like), 2.8 molar equivalents of methanol (the molar equivalents obtained by calculating the free fatty acid in the industrial waste oil as oleic acid) as a reactant, and 3 wt % of solid acid catalyst (the percentage by weight with respect to the industrial waste oil) were mixed in the mixing portion 12. Then, the mixture was supplied to the reactor 13. The supply speed to the reactor 13 was set at about 1.2/h in the space velocity described below. Note that "capacity of reaction unit" in this example refers to a capacity obtained by subtracting the capacity of the unfilled space 22 from the full capacity of the reactor 13.

(Space Velocity)=(Volume Flow Rate of Waste Oil)/(Capacity of Reaction unit)

Figure 6:
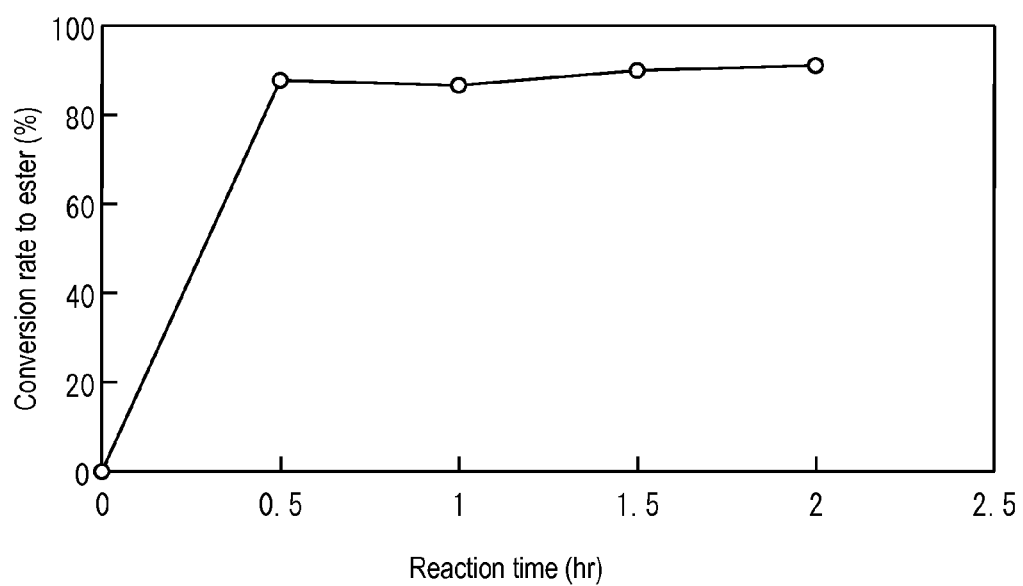
FIG. 6 is a graph showing a conversion rate to ester in an example according to the embodiment.

The microwave power of the reactor 13 was subjected to feedback control based on the temperatures inside the chambers 31 to 34, and, thus, the temperatures of the chambers 31 to 34 were kept constant. In this experiment, the reaction temperature was set at 70° C. FIG. 6 shows a conversion rate to fatty acid methyl ester through the esterification reaction of fatty acid and methanol in this example. The equation for calculating the conversion rate to methyl ester is as follows.

Conversion rate to methyl ester (%)=[Methyl ester concentration]/[Fatty acid initial concentration]×100

As can be clearly seen from FIG. 6, the esterification reaction rapidly progressed after the start of the reaction, and the conversion rate reached 87% in 30 minutes, after which the conversion rate gradually increased, and the reaction reached substantially equilibrium in 1.5 hours. Note that no particular change was seen in the other components in the waste oil. This result shows that, with the flow through-type reaction unit according to this embodiment, the esterification reaction of free fatty acid in waste oil can efficiently progress, and the reaction can stably occur in a continuous manner.

As described above, with the chemical reaction apparatus 1 according to this embodiment, even in the case where the height of the liquid surface increases or decreases according to a change in the amount of the content, the area of the liquid surface does not change, so that the area subjected to microwave irradiation does not change, and the content in the reactor 13 can be efficiently irradiated with microwaves. As a result, the chemical reaction in the reactor 13 can be facilitated. Conventionally, as the horizontal flow-type reactor, a cylindrical reactor in which the length direction matches the flow direction is often used. In such a reactor, the area subjected to irradiation may change according to the height of the liquid surface, resulting in a situation where microwaves cannot be efficiently irradiated. For example, when the liquid surface comes close to the upper end and the unfilled space becomes smaller, the area subjected to microwave irradiation may become smaller, resulting in a situation where the content cannot be efficiently heated. On the other hand, with the reactor 13 according to this embodiment, such a situation can be avoided, and the content can be efficiently heated. Furthermore, since the content inside the reactor 13 is agitated using the agitation units 23, the content can be uniformly irradiated with microwaves even in the case where the depth to which microwaves penetrate is not so deep. Furthermore, since the reactor 13 is partitioned into multiple chambers, the content undergoes a reaction while being retained in each chamber, and, thus, the content can be effectively irradiated with microwaves in each chamber. As a result, a situation can be avoided in which unreacted raw material is discharged from the reactor 13 (i.e., a situation in which the raw material flows in a shortcut from the inlet to the outlet of the reactor 13). Furthermore, if the solid catalyst is microwave-absorbing or microwave-sensitive, the solid catalyst is efficiently heated through microwave irradiation, and, thus, the chemical reaction near the solid catalyst can be facilitated. In this manner, the chemical reaction inside the reactor 13 is facilitated, and, thus, a product material can be more efficiently obtained.

Figure 7:
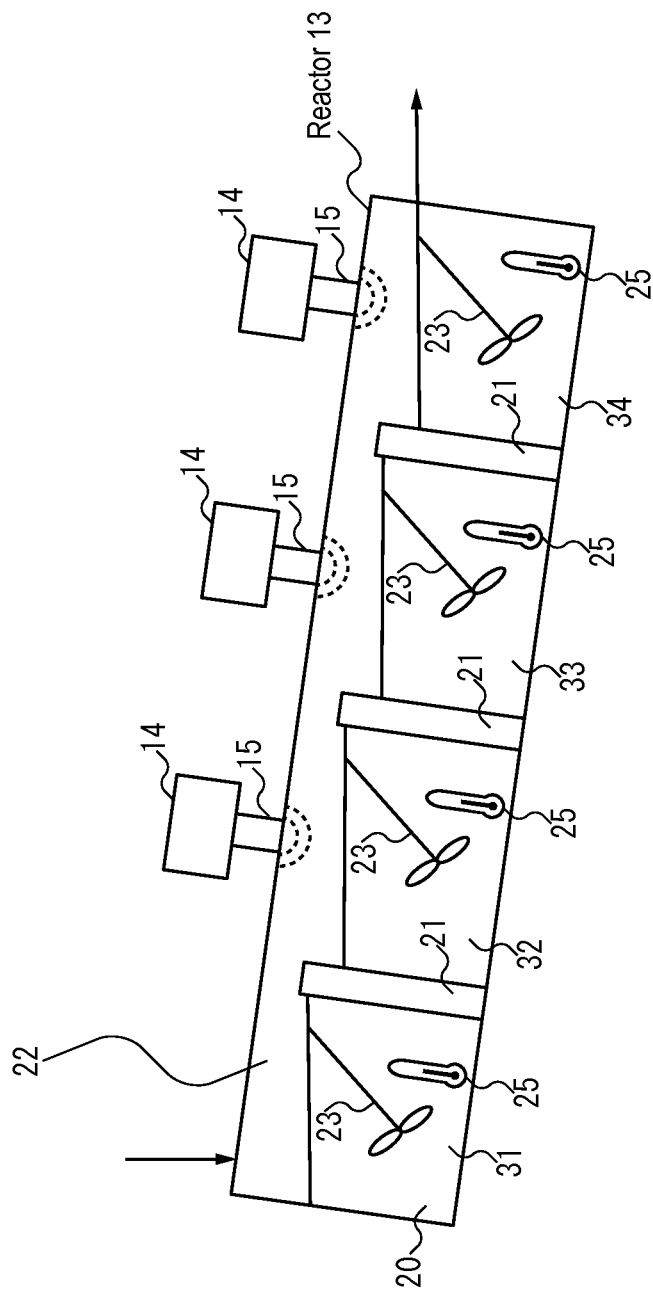
FIG. 7 is a view showing an example of the reactor installed so as to be inclined according to the embodiment.

Note that, in this embodiment, the case has been described where the reactor 13 is installed in the horizontal direction, but there is no limitation to this. As shown in FIG. 7, the reactor 13 may be installed so as to be inclined such that the upstream side is positioned on the upper side and the downstream side is positioned on the lower side. Also in that case, it is preferable that the reactor 13 has a shape in which the area of the liquid surface (in the strict sense, the total area of the liquid surfaces of the chambers) does not change even in the case where the height of the liquid surface changes in each chamber according to a change in the amount of the content. Accordingly, it is preferable that the reactor 13 has a shape in which the cross-section in the liquid surface direction of the content does not change in each chamber as long as the amount of the content is within a predetermined range. Typically, if the reactor 13 has a shape in which the cross-section in the liquid surface direction of the content does not change in a state where the reactor 13 is installed in the horizontal direction, as long as the amount of the content is within a predetermined range, the cross-section in the liquid surface direction of the content tends not to change also in a state where the reactor 13 is installed so as to be inclined. Accordingly, it seems that, as long as the reactor 13 has a shape in which the cross-section in the liquid surface direction of the content does not change in a state where the reactor 13 is installed in the horizontal direction, typically, the area of the liquid surface does not change according to a change in the amount of the content also in a state where the reactor 13 is installed so as to be inclined.

Furthermore, even in the case where the reactor 13 is set in the horizontal direction, it is possible to allow the content to readily flow, by reducing the height of the partition plates 21 from the upstream side toward the downstream side. Also in that case, it is preferable that the reactor 13 has a shape in which the area of the liquid surface (in the strict sense, the total area of the liquid surfaces of the chambers) does not change even in the case where the height of the liquid surface changes in each chamber according to a change in the amount of the content. Accordingly, it is preferable that the reactor 13 has a shape in which the cross-section in the liquid surface direction of the content does not change in each chamber as long as the amount of the content is within a predetermined range.

In this embodiment, the case has been mainly described where the reactor 13 in which the area of the liquid surface does not change according to a change in the amount of the content is shaped such that the side face of the reactor 13 extends in the normal direction of the liquid surface as shown in FIGS. 3A and 3B, but there is no limitation to this. The reactor 13 may have a shape in which the area of the liquid surface does not change according to a change in the amount of the content also in the case where the side face of the reactor 13 extends in a direction different from the normal direction of the liquid surface. This configuration is realized, for example, in the case where the reactor 13 is installed so as to be inclined as shown in FIG. 7.

Furthermore, in this embodiment, the case has been described where the reactor 13 has a shape in which the cross-section in the liquid surface direction of the content does not change as long as the amount of the content is within a predetermined range, but there is no limitation to this. If the reactor 13 has a shape that ultimately prevents the area of the liquid surface from changing according to a change in the amount of the content as long as the amount of the content is within a predetermined range, it is not necessary that the cross-section in the liquid surface direction of the content does not change. Specifically, even in the case where the cross-section in the liquid surface direction of the content changes from one shape (e.g., rectangle, etc.) to another shape (e.g., trapezoid, etc.) according to the height of the liquid surface, as long as the cross-sectional area in the liquid surface direction of the content is the same throughout the height of the liquid surface, it can be said that the reactor 13 has a shape in which the area of the liquid surface does not change according to a change in the amount of the content even in the case where the cross-section in the liquid surface direction of the content changes.

Figure 3C:
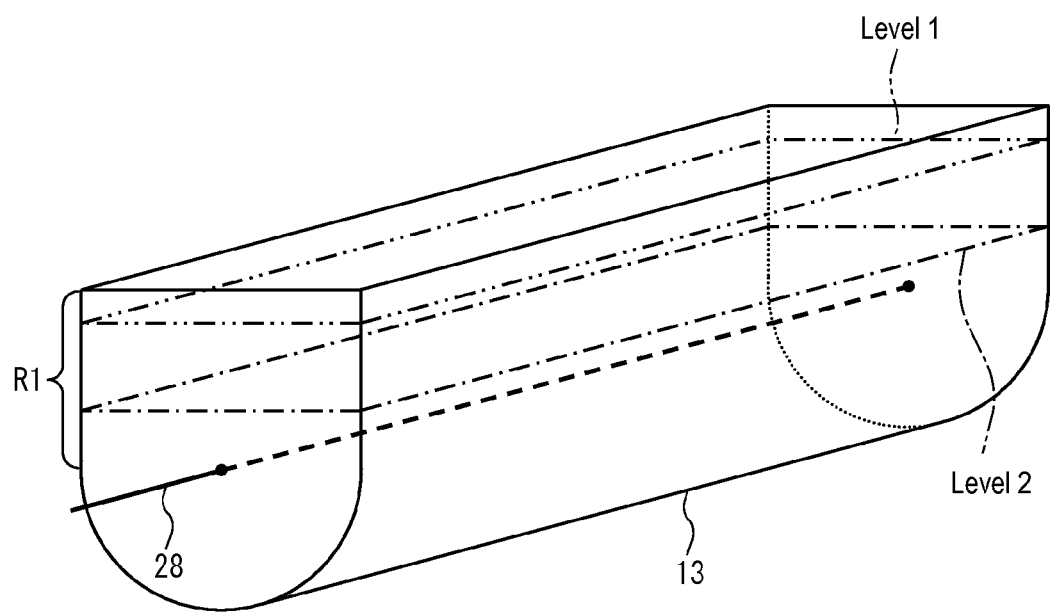
FIG. 3C is a perspective view showing an exemplary shape of the reactor according to the embodiment.
Figure 3D:
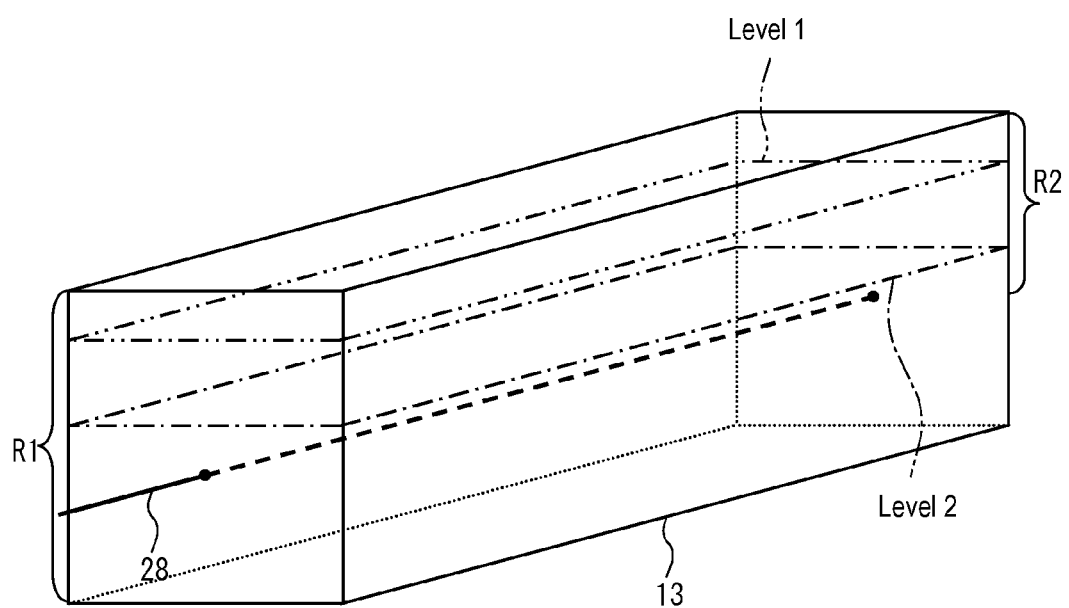
FIG. 3D is a perspective view showing an exemplary shape of the reactor according to the embodiment.

Furthermore, the case has been described with reference to FIG. 2 where each chamber has the agitation unit 23, but there is no limitation to this. Multiple chambers may have a single or multiple agitation units 23. If the chemical reaction apparatus 1 has a single agitation unit 23, as described above, the agitation unit 23 may have a shaft (rotational shaft) shared by multiple chambers. In that case, the agitation unit 23 may include a rotational shaft, multiple rotatable members, and a rotating unit. The rotational shaft is a shaft extending in the flow direction of the reactor 13. For example, in FIG. 2, the rotational shaft may extend from the left end face to the right end face of the reactor 13. The rotational shaft may be provided in parallel to the bottom face of the reactor 13. For example, this rotational shaft may be made of a microwave-transmitting material, a microwave-absorbing material, a microwave-reflecting material, or a combination of two or more freely selected from these materials. If the rotational shaft is made of a microwave-reflecting material (e.g., metal, etc.), microwaves irradiated on the rotational shaft are reflected. Accordingly, if the rotational shaft is present above the liquid surface of the content inside the reactor 13 in this case, part of the microwaves is reflected by the rotational shaft and is not irradiated on the content. Accordingly, in order to avoid such a situation, it is preferable that the liquid surface of the content is positioned above the rotational shaft, that is, the rotational shaft is present inside the content. Furthermore, if the rotational shaft is made of a microwave-absorbing material, microwaves irradiated on the rotational shaft are absorbed. Accordingly, if the rotational shaft is present above the liquid surface of the content inside the reactor 13 in this case, part of the microwaves is absorbed by the rotational shaft and is not irradiated on the content. Furthermore, the heat of the rotational shaft may abnormally increase. Accordingly, in order to avoid such a situation, it is preferable that the liquid surface of the content is positioned above the rotational shaft, that is, the rotational shaft is present inside the content. Accordingly, the amount of the content may be controlled such that the liquid surface of the content is above the rotational shaft, or the reactor 13 may have a shape in which the cross-sectional area in the liquid surface direction does not change at least above the rotational shaft. For example, as shown in FIG. 3C, the height of the liquid surface at the lowest level in the range R1 in which the area of the liquid surface does not change may be set to the height at which the content just covers a rotational shaft 28. Accordingly, if the liquid surface is within the range R1, the area of the liquid surface does not change, and the liquid surface is positioned above the rotational shaft 28. Note that, in FIG. 3C, the radius of the semicylindrical shape forming the lower portion of the reactor 13 is preferably in accordance with the rotational radius of the rotatable members rotating about the rotational shaft 28. This configuration can effectively prevent a situation in which part of the content at the bottom of the reactor 13 fails to be agitated. Furthermore, for example, in the case of the reactor 13 shown in FIG. 3D in which the area of the liquid surface does not change as long as the height of the liquid surface of the content is within the range R1, which covers the entire height, the control can be performed such that the area of the liquid surface does not change, and such that the liquid surface is positioned above the rotational shaft 28, by keeping the height of the liquid surface within the range R2. The height of the liquid surface at the lowest level in the range R2 is set to the height at which the content just covers the rotational shaft 28. Note that "above" and "below" are directions along the vertical direction. The same is applicable to "upper side" and "lower side". Furthermore, "vertical direction" is a direction perpendicular to the horizontal plane. The flow direction in the reactor 13 is the flow direction of the content in the reactor 13, and is typically the same as the length direction of the reactor 13. The rotatable members are members that rotate about the rotational shaft. When the rotatable members rotate, the content is rotationally agitated. The rotatable members may be, for example, blade-like members, wing-like members, rod-like members, or the like, as described above. Furthermore, each chamber may have such a rotatable member, but there is no limitation to this. There may be a chamber having no rotatable member. Furthermore, one chamber may have two or more rotatable members. It is sufficient that the agitation units 23 have at least one or more rotatable members. The rotating unit rotates each rotatable member. If the rotatable members are fixed to the rotational shaft, the rotating unit may be a unit for rotating that rotational shaft. In that case, the rotating unit may be, for example, a motor, an engine, or the like. Furthermore, the rotational shaft may not rotate, but may support the rotatable member in a rotatable manner. In that case, for example, the rotating unit may rotate a rotatable member having a magnet, using a magnetic force. Specifically, as in the case of a motor that rotates a rotor configured by a permanent magnet, using a stator configured by an electromagnet provided around the rotor, it is possible to rotate the rotatable member (rotor) using the rotating unit (stator). Note that, in that case, the rotating unit that is a stator is preferably disposed outside the reactor 13, but there is no limitation to this. The reason for this is that, depending on the material forming the reactor 13, the rotating unit that is a stator cannot be disposed outside the reactor 13. Furthermore, if the agitation units 23 have a rotational shaft extending in multiple chambers, holes through which the rotational shaft extends may be formed in the partition plates 21, or the rotational shaft may extend through recesses or the voids 27 forming the flow paths. Note that, even in the case where the reactor 13 is inclined as shown in FIG. 7 and the agitation units 23 have a rotational shaft extending in multiple chambers, the rotational shaft can be said to extend in the flow direction in the reactor 13. The reason for this is that, although the content seems to horizontally flow in each chamber, the content of the reactor 13 on the whole flows in the length direction of the reactor 13. Accordingly, in this case, the direction in which the rotational shaft extends is different from the liquid surface direction. Furthermore, for example, the position of the outlet of the reactor 13 may be positioned above the rotational shaft such that the liquid surface of the content is positioned above the rotational shaft.

Furthermore, in this embodiment, there is no limitation on the number of rotational shafts or rotating units in the agitation units 23. For example, a single rotational shaft and a single rotating unit may be used to rotate one or more rotatable members, or two or more rotational shafts and two or more rotating units may be used to rotate two or more rotatable members.

In this embodiment, the case has been described where the mixing portion 12 that mixes the raw material and the catalyst is provided, but there is no limitation to this. For example, if a premixure of the raw material and the catalyst is used, if the mixing is also performed by the reactor 13, if the solid catalyst that flows inside the reactor 13 is retained in the reactor 13, or if a solid catalyst forming a fixed bed is used instead of the solid catalyst that flows inside the reactor 13, the chemical reaction apparatus 1 does not have to be provided with the mixing portion 12. Note that, if a solid catalyst forming a fixed bed is used, typically, the solid catalyst forming a fixed bed is provided inside the reactor 13. The solid catalyst forming a fixed bed may be fixed, for example, by being pasted on the inner wall of the reactor 13, or by being placed in a catalyst filled layer, a column, or the like inside the reactor 13. Examples of the shape of the solid catalyst include various grains, a cylinder (that may or may not be hollow), a sphere, a pellet, a ring, a shell, a honeycomb, a foam, a fiber, a cloth, a plate, and other shapes.

Furthermore, in this embodiment, the case has been described where the reactor 13 has four chambers 31 to 34 that are continuously arranged in series as shown in FIG. 2, but there is no limitation on the number of chambers. Typically, as the number of chambers increases, a situation can be more effectively prevented in which the raw material flows in a shortcut from the inlet to the outlet of the reactor 13. Furthermore, if the capacity of each chamber does not change regardless of an increase or a decrease in the number of chambers, the retention time from when the content of the reactor 13 flows into the reactor 13 to when the content flows out of the reactor 13 becomes longer as the number of chambers increases, and the retention time becomes shorter as the number of chambers decreases. Accordingly, in this case, the number of chambers can be adjusted such that a desired retention time is obtained.

Figure 8:
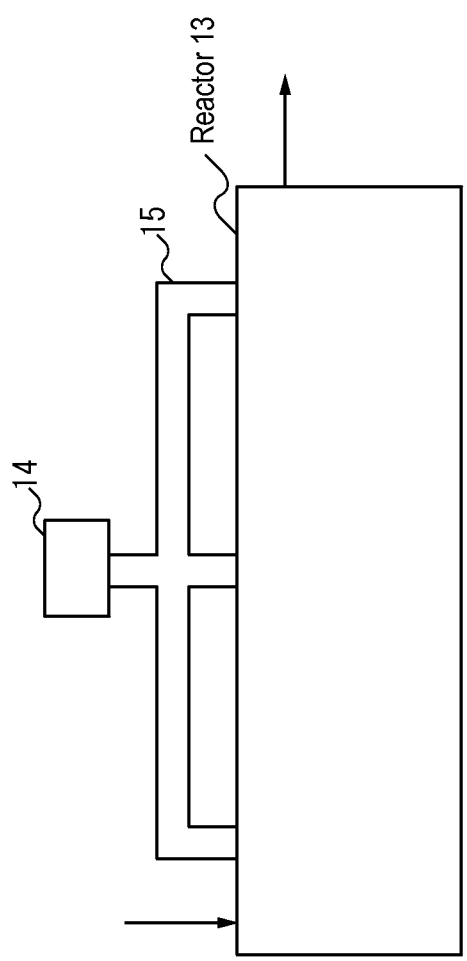
FIG. 8 is a view showing another exemplary microwave generator and waveguide according to the embodiment.

Furthermore, in this embodiment, the case has been described where the multiple microwave generators 14 are provided, but there is no limitation to this. For example, the microwaves generated by the microwave generator 14 may be transmitted via a branched waveguide 15 to multiple locations as shown in FIG. 8. The multiple locations may be, for example, multiple chambers. FIG. 8 shows the case in which the chemical reaction apparatus 1 is provided with only one microwave generator 14, but, in the case where the chemical reaction apparatus 1 is provided with two or more microwave generators 14, the microwaves generated by any one of the multiple microwave generators 14 may be transmitted via the branched waveguide 15 to multiple locations. For example, if the microwaves generated by the microwave generator 14 are transmitted to multiple chambers, the microwave control portion 16 may control the power of that microwave generator 14 using any or all of the temperatures of the chambers to which the microwaves generated by the microwave generator 14 are transmitted. For example, the microwave control portion 16 may perform the control using an average of all temperatures of the chambers, or may perform the control using a maximum value or a minimum value of the temperatures of the chambers.

Furthermore, in this embodiment, the case has been described where the chemical reaction apparatus 1 is provided with the temperature measuring portions 25 and the microwave control portion 16, but there is no limitation to this. For example, if it is possible to keep the temperature inside the reactor 13 at a desired temperature or in a desired temperature range by setting the power of microwaves to a predetermined value, the control of the power of microwaves using the temperature does not have to be performed.

Furthermore, in this embodiment, the case has been described where the catalyst separating portion 17 is provided on the path after the reactor 13, but there is no limitation to this. If the catalyst does not have to be separated by the chemical reaction apparatus 1 according to this embodiment, as in the case in which the catalyst is separated by another apparatus, the case in which the solid catalyst that flows inside the reactor 13 is retained in the reactor 13, the case in which a solid catalyst forming a fixed bed is used instead of the solid catalyst that flows inside the reactor 13, or the case in which no catalyst is used in the chemical reaction in the reactor 13, the catalyst separating portion 17 does not have to be provided.

Furthermore, in this embodiment, the case has been described where the raw material and the catalyst are mixed and loaded into the reactor 13, but there is no limitation to this. For example, only the raw material may be loaded into the reactor 13. Furthermore, if the raw material and the catalyst are not mixed, only the raw material may flow inside the reactor 13. That is to say, the content of the reactor 13 may be, for example, a mixture of multiple raw materials. Furthermore, even in the case where the raw material and the catalyst are not mixed, for example, the raw material and the catalyst may flow inside the reactor 13 when the solid catalyst that flows inside the reactor 13 is retained in the reactor 13. Furthermore, if the raw material and the catalyst are not mixed, the mixing portion 12 may, for example, mix the raw material, or mix the raw material (substrate) and the reactant. Furthermore, if the raw material and the like do not have to be mixed, the chemical reaction apparatus 1 does not have to be provided with the mixing portion 12 as described above.

Furthermore, in this embodiment, the case has been described where one or more agitation units 23 that agitate the raw material inside the reactor 13 are provided, but there is no limitation to this. For example, if the reactor 13 is configured such that the entire raw material can be easily irradiated with microwaves (e.g., if the inner diameter of the reactor 13 is small, etc.), the agitation units 23 do not have to be provided.

Furthermore, in this embodiment, the case has been described where the chemical reaction apparatus 1 is provided with the treated liquid storage tank 18, but there is no limitation to this. For example, a mixture of the product material and the by-product discharged from the chemical reaction apparatus 1 may be subjected to extraction of the product material and the like in another apparatus.

Figure 9A:
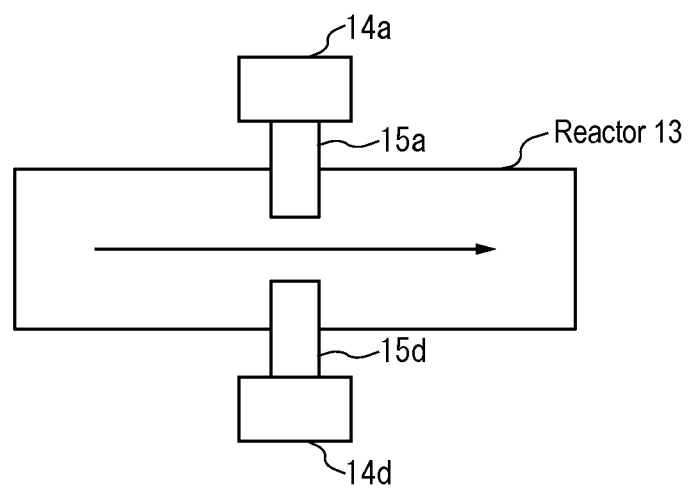
FIG. 9A is a view illustrating a position for microwave irradiation according to the embodiment.
Figure 9B:
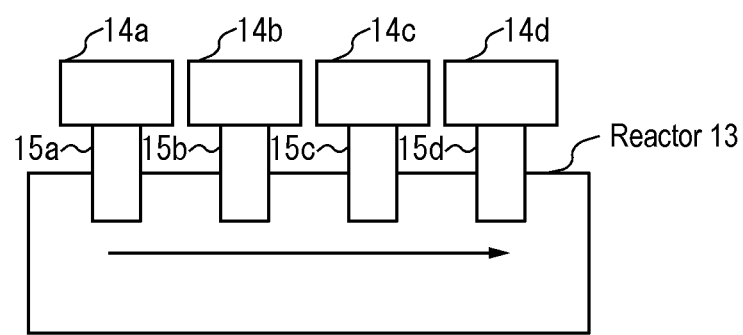
FIG. 9B is a view illustrating positions for microwave irradiation according to the embodiment.

Furthermore, in this embodiment, the chemical reaction apparatus 1 may be provided with two or more microwave generators 14, and the two or more microwave generators 14 may generate microwaves having two or more frequencies. That is to say, the content of the reactor 13 may be irradiated with microwaves having two or more frequencies. In that case, the microwaves having two or more frequencies may be irradiated on the same position, or may be respectively irradiated on different positions. For example, as shown in FIG. 9A, microwaves having frequencies X and Y respectively generated by microwave generators 14a and 14d may be irradiated on the same position in the reactor 13, that is, at the midstream in the reactor 13. Note that the microwaves having the frequencies X and Y are respectively transmitted via waveguides 15a and 15d to the reactor 13. Furthermore, for example, as shown in FIG. 9B, microwaves having a frequency X generated by microwave generators 14a, 14b, and 14c may be irradiated on the side from the upstream to the midstream in the reactor 13, and microwaves having a frequency Y generated by a microwave generator 14d may be irradiated on the downstream side in the reactor 13. Note that the microwaves having the frequency X are respectively transmitted via waveguides 15a, 15b, and 15c to the reactor 13. Furthermore, the microwaves having the frequency Y are transmitted via a waveguide 15d to the reactor 13. FIGS. 9A and 9B are both views of the reactor 13 from above, wherein the arrows in the drawings indicate the flow of the content inside the reactor 13. If microwaves having two or more frequencies are irradiated, the number of frequencies may be two, or three or more. There is no limitation on the combination of two or more frequencies, as long as they are selected from the range from 300 MHz to 300 GHz. For example, if microwaves having two frequencies are irradiated, examples of the combination of these frequencies include 2.45 GHz and 5.8 GHz, 2.45 GHz and 24 GHz, 2.45 GHz and 913 MHz, 5.8 GHz and 24 GHz, 5.8 GHz and 913 MHz, and 24 GHz and 913 MHz. Furthermore, if microwaves having two or more frequencies are irradiated, there is no limitation on the irradiation timing. For example, microwaves having two or more frequencies may be simultaneously irradiated, or may be irradiated respectively in different irradiation periods. For example, in the latter case, microwaves having the frequency X may be irradiated in one period, and microwaves having the frequency Y may be irradiated in the next period. Furthermore, if microwaves having two or more frequencies are irradiated, the microwaves having two or more frequencies may be introduced to one unfilled space 22, or may be introduced to different unfilled spaces 22. In the latter case, there are at least two or more unfilled spaces 22 that have been separated from each other by the partition plate 21 inside the reactor 13. Note that if microwaves having two or more frequencies are irradiated, a material that is not affected by the action (e.g., heating, etc.) of microwaves having one frequency can be also affected, and, thus, a wider range of materials can be affected by the microwaves.

Furthermore, in the foregoing embodiment, information relating to the processing performed by each constituent element, for example, information that is to be accepted, acquired, selected, produced, transmitted, or received by each constituent element, information such as a threshold value, a numerical expression, or an address used in each constituent element in the processing and the like may be retained in an unshown storage medium temporarily or for a long period of time even if not specified in the description above. Furthermore, information may be accumulated in the unshown storage medium by each constituent element or by an unshown accumulating unit. Furthermore, information may be read from the unshown storage medium by each constituent element or by an unshown reading unit.

Furthermore, in the foregoing embodiment, if information used in each constituent element or the like, for example, information such as a threshold value, an address, or various setting values used in each constituent element in the processing may be changed by a user, the user may change such information as appropriate even if not specified in the description above, but there is no limitation to this. If the user may change such information, the change may be realized by, for example, an unshown accepting unit that accepts a change instruction from the user and an unshown changing unit that changes information according to the change instruction. The change instruction may be accepted by the unshown accepting unit, for example, by accepting information from an input device, by receiving information transmitted via a communication line, or by accepting information read from a predetermined storage medium.

Furthermore, in the foregoing embodiment, each constituent element may be configured by dedicated hardware, or, alternatively, constituent elements that can be realized by software may be realized by executing a program. For example, each constituent element may be realized by a program execution unit such as a CPU reading and executing a software program stored in a storage medium such as a hard disk or a semiconductor memory.

Furthermore, it will be appreciated that the present invention is not limited to the embodiment set forth herein, and various modifications are possible within the scope of the present invention.

INDUSTRIAL APPLICABILITY

As described above, the chemical reaction apparatus according to the present invention is effective in that a raw material and the like can be efficiently irradiated with microwaves, and, thus, it is useful, for example, as a chemical reaction apparatus for performing chemical reaction that requires heating.

The invention claimed is:
1. A chemical reaction apparatus, comprising:
   a horizontal flow reactor inside of which has been partitioned into multiple chambers by a partition plate, and in which a liquid content horizontally flows with an unfilled space being provided thereabove;
   a microwave generator that generates microwaves;

at least one waveguide that transmits the microwaves generated by the microwave generator to the unfilled space in the reactor;
at least one agitation unit that rotationally agitates the content inside the reactor, comprising:
 a rotational shaft that extends in a liquid content flow direction in the reactor;
 at least one rotatable member that is rotated about the rotational shaft; and
 a rotating unit that rotates the at least one rotatable member; and
a reactor outlet disposed at a height above the rotational shaft maintaining a surface of the liquid content above the rotational shaft,
wherein the unfilled space is between the liquid surface and a transmission end of the at least one waveguide,
wherein the unfilled space is continuous over at least two of the multiple chambers, and
wherein the reactor has a shape in which an area of the liquid surface does not change even in a case where a height of the liquid surface changes according to a change in an amount of the content, and
wherein the reactor shape further comprises the area in a liquid surface direction that is unchanging above the rotational shaft.

2. The chemical reaction apparatus according to claim 1, wherein the reactor shape is such that the area of the liquid surface does not change according to the change in the amount of the content, as long as the amount of the content is within a predetermined range.

3. The chemical reaction apparatus according to claim 1, wherein the reactor has, below the rotational shaft, a semicylindrical shape elongated in the flow direction and projecting downward.

4. The chemical reaction apparatus according to claim 1, wherein the reactor can be opened and closed above the unfilled space.

* * * * *